United States Patent
Phillips

(12) 
(10) Patent No.: US 6,312,390 B1
(45) Date of Patent: *Nov. 6, 2001

(54) BREATH TEST FOR DETECTION OF LUNG CANCER

(76) Inventor: Michael Phillips, 1 Horizon Rd., Fort Lee, NJ (US) 07024

(*) Notice: Subject to any disclaimer, the term of this patent is extended or adjusted under 35 U.S.C. 154(b) by 0 days.

This patent is subject to a terminal disclaimer.

(21) Appl. No.: 09/410,870

(22) Filed: Oct. 1, 1999

Related U.S. Application Data

(63) Continuation of application No. 08/951,884, filed on Oct. 16, 1997, now Pat. No. 5,996,586.
(60) Provisional application No. 60/041,380, filed on Mar. 26, 1997.

(51) Int. Cl.⁷ ..................................................... A61B 5/08
(52) U.S. Cl. .................. 600/532; 436/64; 128/206.29; 128/898
(58) Field of Search ............... 128/898, 206.29, 128/204.17; 600/532, 543, 473; 436/64, 96, 813, 900

(56) References Cited

U.S. PATENT DOCUMENTS

| | | | |
|---|---|---|---|
| 4,534,360 | * 8/1985 | Williams | 600/473 |
| 4,772,559 | * 9/1988 | Preti et al. | 436/64 |
| 5,465,728 | * 11/1995 | Phillips | 600/543 |
| 5,996,586 | * 12/1999 | Phillips | 128/898 |

* cited by examiner

Primary Examiner—Eric F. Winakur
Assistant Examiner—Ryan Carter
(74) Attorney, Agent, or Firm—Pitney, Hardin, Kipp & Szuch LLP

(57) ABSTRACT

Carcinogenesis is accompanied by increased production of oxygen free radicals (OFRs) which degrade membranes by lipid peroxidation. The process evolves volatile organic compounds (VOCs), principally alkanes, which are excreted in the breath. VOCs in alveolar breath provided sensitive and specific markers of lung cancer. Breath VOC analysis is a non-invasive test which may potentially detect lung cancer at an early stage and reduce the high mortality of the disease.

4 Claims, 12 Drawing Sheets

BREATH TEST FOR DETECTION OF LUNG CANCER

CROSS-REFERENCE TO RELATED APPLICATION

This application claims the priority of Provisional Application Serial No. 60/041,380 filed Mar. 26, 1997, and a continuation of U.S. patent application Ser. No. 08/951,884 filed Oct. 16, 1997 now U.S. Pat. No. 5,996,586.

BACKGROUND OF THE INVENTION

1. Field of the Invention

The invention relates to methods of detecting and diagnosing lung cancers in mammals.

2. Brief Description of Related Art

Primary carcinoma of the lung is the leading cause of cancer death in the United States. Every year, more than 100,000 males and 50,000 females develop lung cancer, and most of them die within twelve months. There is a clinical need for a screening test which can detect lung cancer in its earliest stages because prompt treatment of localized disease improves the 5-year survival rate to 30% in males and 50% in females. However, most cases are not detected until local or metastatic growth causes symptoms, and prospective screening with frequent radiography and sputum cytology has not improved the survival rate in smoking males aged 45 years or older. Since early detection of lung cancer can potentially reduce mortality, researchers have investigated alternative diagnostic technologies such as breath testing.

The rationale of a breath test for lung cancer is based upon three observations: first, carcinogenesis is accompanied by increased production of oxygen free radicals (OFRs), second, OFRs degrade cell membranes by lipid peroxidation, evolving alkanes such as ethane and pentane, and third, these alkanes are volatile organic compounds (VOCs) which are excreted in the breath.

OFRs cause mutagenesis by oxidative damage to DNA; as a result, affected cells acquire malignant properties and tumor clones expand. The mutagenic effects of OFRs appear to be partially reversible; treatment with OFR scavengers significantly improved survival in metastatic gastric cancer as well as in a rat model of colon cancer induced by 1,2-dimethylhydrazine. Oxidative stress has also been associated with chemical toxicity, ischemia, inflammation and dietary deficiency of antioxidants. The final common pathway is the intracellular accumulation of OFRs which overcome cellular defense mechanisms and degrade cellular membranes by lipid peroxidation, resulting in chemical and anatomical disruption of the membranes which may progress to cell death.

Breath hydrocarbons, particularly alkanes such as pentane, are markers of oxidative stress mediated by OFRs. Increased breath pentane has been reported in breast cancer, acute myocardial infarction, heart transplant rejection, rheumatoid arthritis, and acute bronchial asthma. Previous studies have attempted to identify the VOCs in breath which might provide clinically useful markers of lung cancer. Gordon et al reported 28 VOCs which were present in the breath of more than 90% of patients with lung cancer; and Preti et al found increased o-toluidine;

Preti G, Labows J N, Kostelc J G and Aldinger S: Analysis of lung air from patients with bronchogenic carcinoma and controls using gas chromatography mass spectrometry. J. Chromatography 1988;432:1–11.

Gordon S M, Szidon J P, Krotoszynski B K, Gibbons R D and O'Neill H J: Volatile organic compounds in exhaled air from patients with lung cancer. Clin Chem 1985; 31:1278–82;

O'Neill H J, Gordon S M, O'Neill MH, Gibbons R D and Szidon J P: A computerized classification technique for screening for the presence of breath biomarkers in lung cancer. Clin Chem 1988; 34(8):1613–1618.

However, progress in breath testing for lung cancer has been impeded by the technical difficulty of detecting VOCs in breath. The majority are excreted in very low concentrations: nanomolar ($10^{-9}$ mol/l) or picomolar ($10^{-12}$ mol/l). Most existing laboratory instruments cannot detect VOCs in such low levels in breath unless the sample is concentrated prior to analysis. Researchers have circumvented this problem by constructing specialized instruments for the collection and concentration of breath samples. Phillips has recently described a method for the collection and analysis of breath VOC samples which can be employed in clinical settings. A portable microprocessor-controlled breath collection apparatus collects alveolar breath VOCs onto sorbent traps which are then analyzed by conventional gas chromatography and mass spectroscopy. This breath collection apparatus was utilized to collect samples from patients undergoing bronchoscopy and biopsy for suspected lung cancer, in order to correlate the VOCs in alveolar breath with the histopathologic screening tests.

Phillips M: Method for the collection and assay of volatile organic compounds in breath. Analytical Biochemistry 1997;247:272–278.

SUMMARY OF THE INVENTION

The invention comprises a method of detecting and diagnosing lung cancer in a mammal, including a human, which comprises;

collecting a measured quantity of alveolar breath from the mammal; and analyzing the collected breath for the presence of volatile organic markers for lung cancer;

the detection of volatile organic markers being indicative of the presence of a lung cancer screening test.

The test method is simple, non-invasive and economical as a screening test procedure.

DETAILED DESCRIPTION OF THE INVENTION

Figure 1:
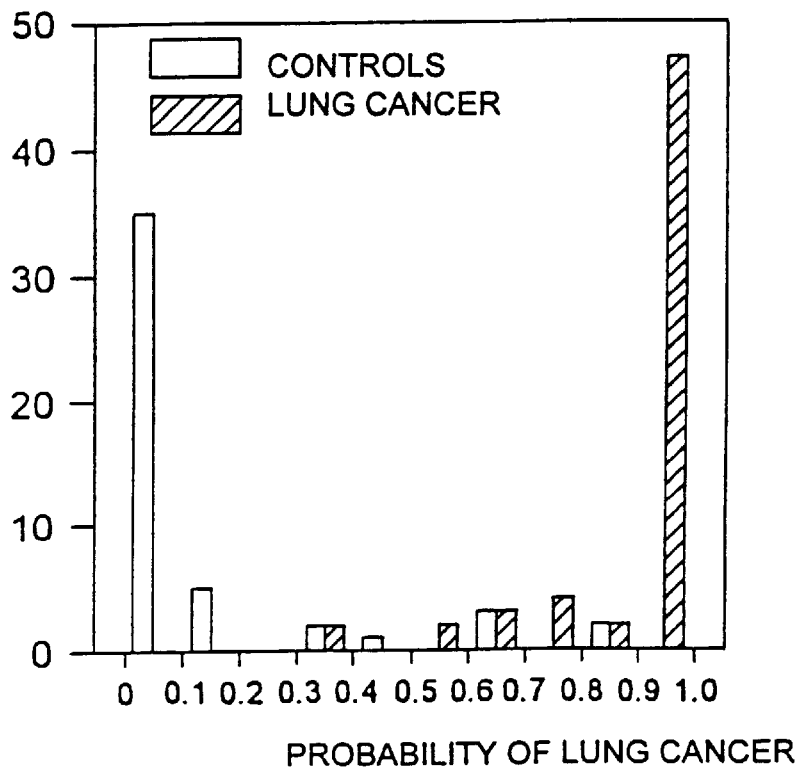
FIG. 1: Results of breath testing in patients with and without lung cancer. The left-hand panel show posterior probability of disease as determined by logistic regression analysis of alveolar gradients of significant VOCs in breath (identified in Table 2). The right-hand panel demonstrates the receiver operating characteristic (ROC) curve of diagnostic sensitivity and specificity of this model.
Figure 1:
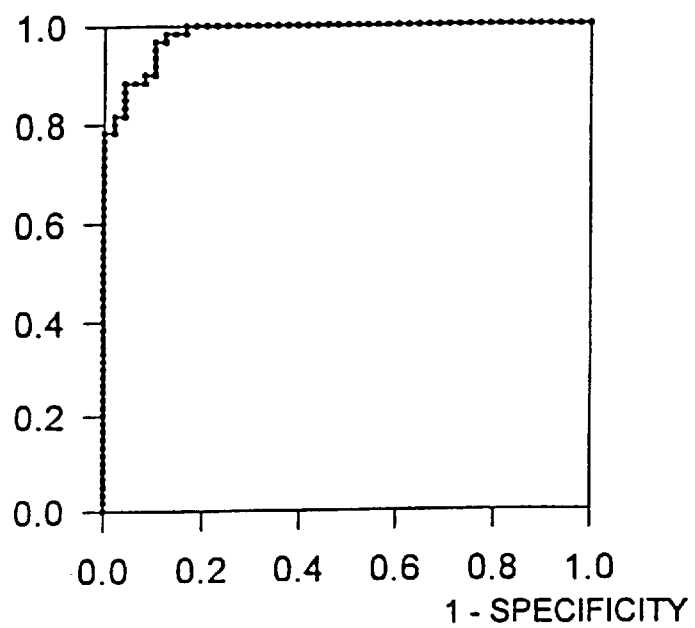

Breath VOC analysis is a non-invasive procedure which opens a window onto the composition of the VOCs circulating in the blood. Like water flowing down a hill, VOCs flow down the concentration gradient from blood into breath (or vice versa) by rapid diffusion across the pulmonary alveolar membrane. Breath tests are potentially more sensitive than blood tests because the quantity of collected analysis is limited only by the capacity of the breath collection apparatus and the patience of the donor. Breath testing was pioneered in the eighteenth century by Lavoisier; his discovery that humans and animals excrete carbon dioxide in their breath was the first evidence for oxidative metabolism of foodstuffs. Nineteenth century researchers reported breath tests for ethanol and for elevated acetone in uncontrolled diabetes mellitus. The modern era of breath testing dates from 1971, when Linus Pauling and his colleagues discovered that a sample of concentrated human breath contained several hundred VOCs when analyzed by gas chromatography.

Alveolar gradients of a number of the VOCs in Table 2 (below) were significantly lower or more negative in the cancer patients than in the controls. This apparently paradoxical finding is consistent with the observations of Khyshiktuev et al, who also detected a reduction in breath markers of lipid peroxidation in patients with lung cancer. The simplest hypothesis which might account for these findings is that lung cancer is associated with an increased rate of metabolism and/or excretion of alkanes and their derivatives. Breath VOCs excreted in vivo are the product of a number of interacting kinetic processes: absorption, distribution, metabolism (anabolism and catabolism) and excretion. Hence, alkanes produced in the lung by cancer cells may be catabolized and excreted in the lung or at other sites. Pentane is metabolized in vivo by the cytochrome P-450 system, a pathway which can be induced by phenobarbital and inhibited by cimetidine. Radiolabelled ethane and pentane are both metabolized to $CO_2$. Several studies have confirmed increased cytochrome P450 activity in cancer, which is known to cause carcinogen activation and correspondingly increased cancer risk in animal models. Drugs such as phenobarbital which induce increased cytochrome P450 activity also induce hepatic carcinogenesis in animals.

Since the number of breath VOCs exceeded the number of subjects, there is a risk that some of the VOCs in Table 2 may have been selected as markers of lung cancer by chance alone. However, this is not likely for at least three reasons:

First, there is the internal evidence of structural clustering of VOCs. Several of the VOCs were structurally similar to one another e.g. eight were derivatives of cyclohexane, four of nonane, three each of heptane, pentane and hexane. This is unlikely to have occurred by chance, and is consistent with an abnormality in alkane metabolism resulting in altered production of a number of closely related compounds in the same metabolic pathway.

Second, the majority of the significant VOCs in patients with lung cancer were either methylated alkanes or their derivatives, which is consistent with the hypothesis that they represent lipid peroxidation products of OFR activity. VOCs were predominantly derivatives of ethane, propane, pentane, hexane, heptane, octane and nonane.

Third, nine of the significant VOCs in patients were similar to those reported by Gordon et al as markers of lung cancer (O'Neil, H. J., et al. supra.) with comparatively minor differences in chemical structure which may be attributable to the use of different libraries of mass spectra. An isoprenoid breath VOC reported by O'Neil, et al as a possible shunt pathway in sterol metabolism, 1-methyl-4-(1-methylethenyl) cyclohexene was also identified as a significant VOC in patients with lung cancer.

We conclude that breath VOC analysis is a non-invasive test which can detect lung cancer with high sensitivity and specificity. If these findings are confirmed in validation studies, breath testing might be employed as a new screening test to identify patients with early stage lung cancer, and potentially improve their prospects of survival.

Human Subjects: Breath samples were collected from patients prior to bronchoscopy in the pulmonary medicine services of two academic medical centers: Penn State Medical Center (the Milton S Hershey Medical Center, Hershey, Pa.) and the Royal Postgraduate Medical School (London, England). Patients were included if they were aged over 18, able to understand the breath collection procedure, give signed informed consent, and were scheduled for bronchoscopy for evaluation of a suspicious x-ray in order to confirm or exclude lung cancer. A "suspicious x-ray" was defined as the presence of a lung mass, or a lung infiltrate with volume loss suggestive of endobronchial tumor. Patients were excluded if previous investigations had confirmed a neoplasm of the lung or of some other site. The research was approved by the institutional review boards of all participating institutions.

Bronchoscopy and Biopsy: Bronchoscopy was performed according to standard procedures. Following premedication with intramuscular meperidine and atropine, the patient's nose, nasopharynx, and oropharynx was sprayed with a 1% lidocaine solution. The bronchoscope was then passed through the most patent nare through the upper airway and into the tracheo-bronchial tree. Intraluminal lesions were ravaged or brushed for cytology, and directly biopsied using a standard alligator forceps. Parenchymal lesions were evaluated by lavage of the appropriate airway segment and by transbronchial biopsy under direct fluoroscopic guidance. Lung biopsy specimens were preserved in formalin for microscopic examination by a pathologist.

Collection of Breath VOCs: The method has been described (Phillips, M., supra). A portable breath collecting apparatus as described in U.S. Pat. No. 5,465,728, incorporated herein by reference thereto was employed to collect breath VOCs onto sorbent traps. Subjects sat in front of the apparatus wearing a nose clip, breathing in and out through a disposable mouthpiece. Alveolar breath was sampled at 2.0 liters/min for 5.0 min and drawn through a sorbent trap which captured the VOCs. A sample of ambient room air was collected in a similar fashion onto another sorbent trap. Traps were stored in hermetically sealed containers in order to prevent sample loss or contamination.

Analysis of Breath VOCs: The method has been described (Phillips, M., supra). Using automated instrumentation, breath VOCs were thermally desorbed from the sorbent trap, concentrated by two-stage cryofocusing, separated by gas chromatography, then quantified and identified by mass spectroscopy. A typical chromatogram of an alveolar breath sample yielded 150–250 different VOCS, all of which were automatically identified and quantified. The chemical structure of each VOC was tentatively identified from its mass spectrum, utilizing a computer-based library. Each VOC was quantified by measuring the area under curve (AUC) of the chromatographic peak, and calculating the ratio of the AUC to the AUC of a standard.

Blinding Procedures: The breath samples were analyzed without knowledge of the bronchoscopy or biopsy findings. Neither the physicians who performed the bronchoscopies nor the pathologists who evaluated the biopsy specimens had any knowledge of the results of the breath test.

Analysis of Data: The alveolar gradient of each VOC was determined as the concentration in alveolar breath minus the concentration in inspired air i.e. alveolar gradient=$AUC_{VOC\ in\ breath}/AUC_{standard} - AUC_{VOC\ in\ air}/AUC_{standard}$. The alveolar gradients of all VOCs detected in at least three breath samples were compared in subjects with and without lung cancer. Since the number of variables (breath VOCs) exceeded the number of subjects, alveolar gradients were screened first by Student's test and then by factor analysis. Forward-stepwise discriminant analysis was used to identify VOCs that could discriminate between patients with and without lung cancer. The independent variable was the clinical stage of lung cancer, and the dependent variables were the alveolar gradients of a breath VOC found in more than 50% of all patients. The relative contribution of each VOC in the model was ranked by partial Wilks' lambda. The final model was then used to calculate the posterior probability of lung cancer in each subject from the breath sample. Discriminant analysis was also used to compare predictive values from the model with those based on demographic factors (age, tobacco smoking, and sex). A cross-validation of the patients classification was done by the SPSS "leave one out" discriminant analysis procedure which predicted whether a patient belonged to the group with or without lung cancer, based on the breath VOC model derived from all the other patients in the study.

RESULTS

Human subjects: 108 subjects were studied and none experienced any adverse effects of the breath test. Lung cancer was confirmed histologically in 60 and excluded in 48. Characteristics of the subjects and their diagnoses are shown in Table 1, below.

TABLE 1

| | Hershey | London | Total |
|---|---|---|---|
| Number of patients | 73 | 35 | 108 |
| Sex (M/F) | 43/30 | 20/15 | 108 |
| Smoking status: | | | |
| non-smoker | 13 | 4 | 17 |
| smoker | 17 | 14 | 31 |
| ex-smoker | 43 | 17 | 60 |
| Age: mean (SD) | 63.6 (12.1) | 65.7 (15.3) | 64.3 (13.2)NS |
| Cancer type small cell | 7 | 3 | 10 |
| non-small cell: all | 30 | 20 | 50 |
| epidermoid | 12 | 12 | 24 |
| adenocarcinoma | 15 | 8 | 23 |
| large cell | 1 | 0 | 1 |
| mesothelioma | 1 | 0 | 1 |
| melanoma 1 | 0 | 1 | |
| Stage of cancer | | | |
| 0 | 36 | 12 | 48 |
| X | 2 | 1 | 3 |
| I | 4 | 5 | 9 |
| II | 2 | 1 | 3 |
| IIIa | 5 | 6 | 11 |

TABLE 1-continued

| | Hershey | London | Total |
|---|---|---|---|
| IIIb | 6 | 1 | 7 |
| IV | 18 | 9 | 27 |

Figure 2:
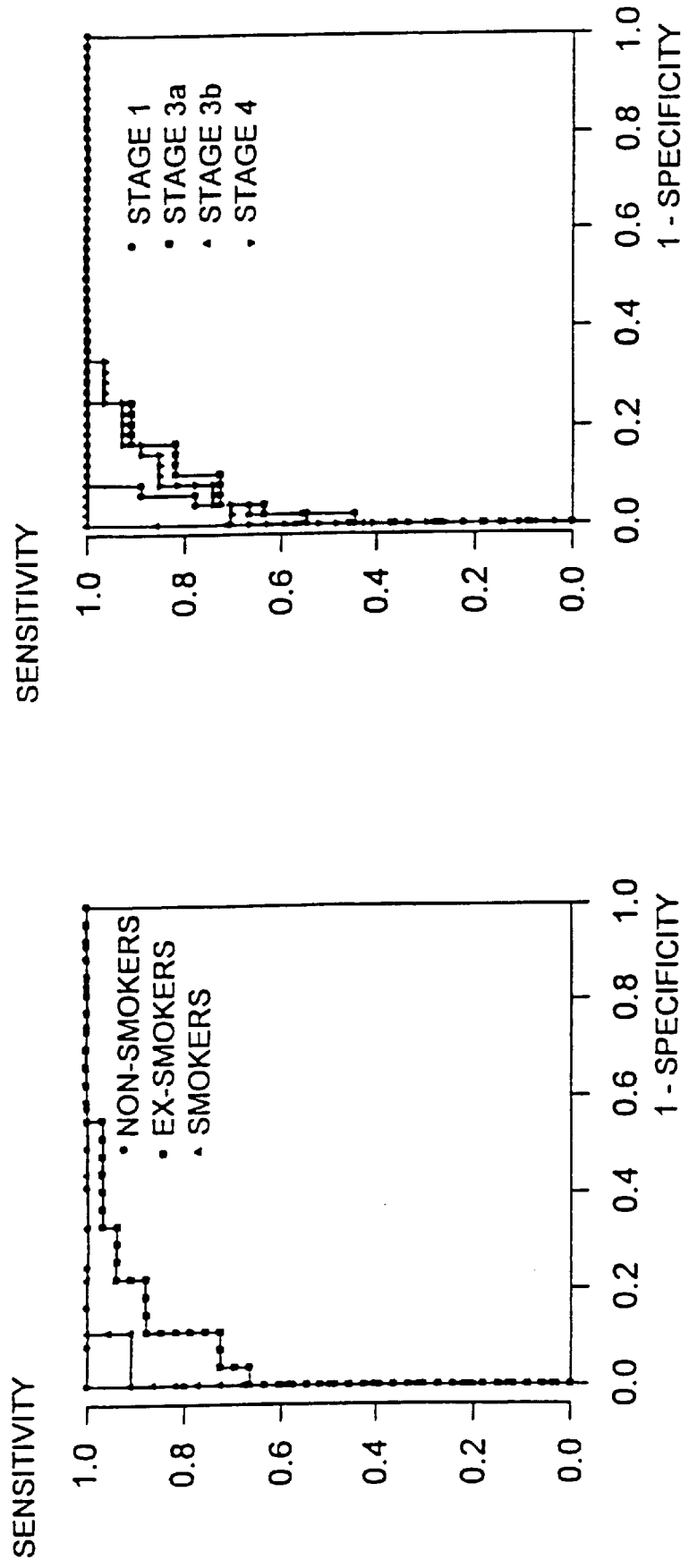
FIG. 2: Performance of the breath test in subgroups. ROC curves demonstrate the sensitivity and specificity of the test according to smoking behavior, stage of the lung cancer, adenocarcinoma versus epidermoid carcinoma, small cell versus non-small cell carcinoma, age and sex.
Figure 2:
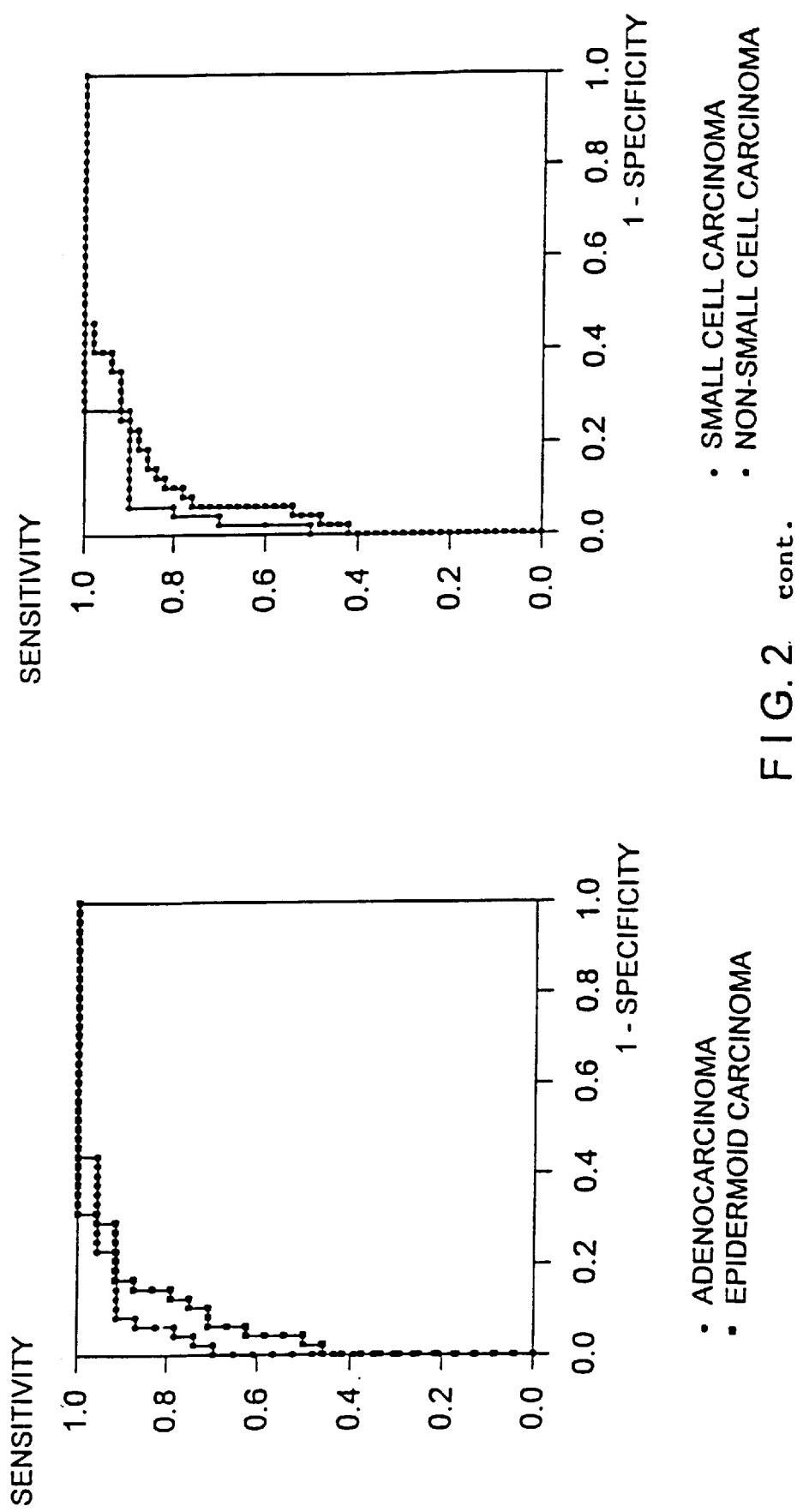
Figure 2:
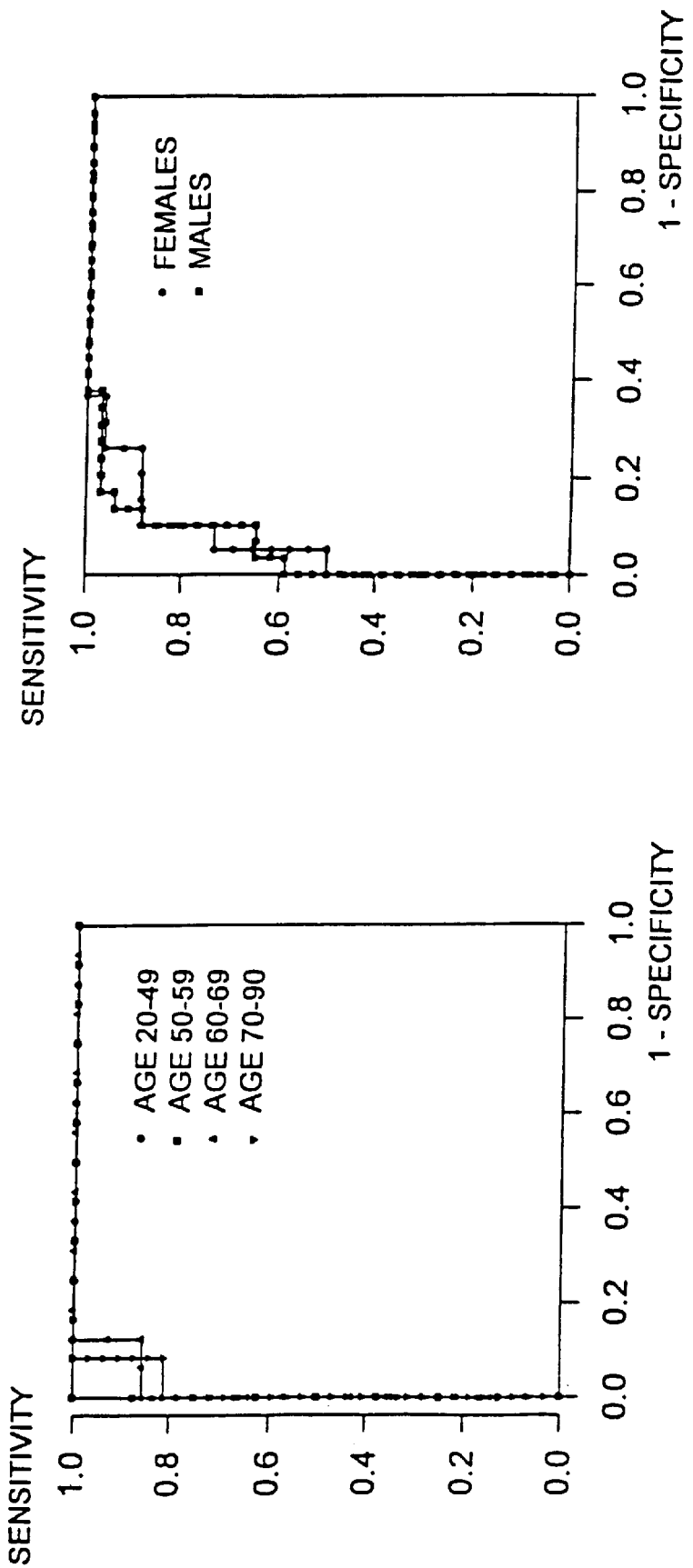

Breath VOC Analysis 1124 different VOCs were observed in three or more samples of alveolar breath. The mean alveolar gradients of 22 VOCs, predominantly methylated alkanes, were significantly different in subjects with lung cancer (Table 2 below). The posterior probability of lung cancer in patients with and without disease, and the receiver operating characteristic (ROC) curve of sensitivity and specificity of the breath test are shown in FIG. 1. At the shoulder of the curve, the test exhibited 93.3% sensitivity and 91.7% specificity. With 100% sensitivity, the test was 75.0% specific; with 100% specificity, the test was 88.3% sensitive. The sensitivity and specificity of the test in subgroups is shown in FIG. 2, in ROC curves for smoking status, stage of cancer, cancer cell type (epidermoid versus adenocarcinoma, small-cell versus non small-cell carcinoma), age and sex.

TABLE 2

Styrene (ethenylbenzene)
Heptane, 2,2,4,6.6-pentamethyl
Heptane, 2-methyl
Decane
Benzene, propyl-
Undecane
Cyclopentane, methyl-
Cyclopropane 1-methyl-2-pentyl-
Methane, trichlorofluoro-
Benzene
Benzene, 1,2,4-trimethyl-
1,3-butadiene, 2-methyl-(isoprene)
Octane. 3-methyl-
1-hexene
Nonane. 3-rnethyl-
1-heptene
Benzene, 1,4-dimethyl
Heptane 2,4-dimethyl
Hexanal
Cyclohexane
Benzene, 1-methylethenyl-
Hepatanal We further evaluated the breath test in the lung cancer study by comparing the breath alkane profiles in subjects with and without cancer, in combination with methylalkanes in the breath. Logistic regression analysis was employed to determine the probability of lung cancer based on the alveolar gradients of these VOCs.

Figure 3A:
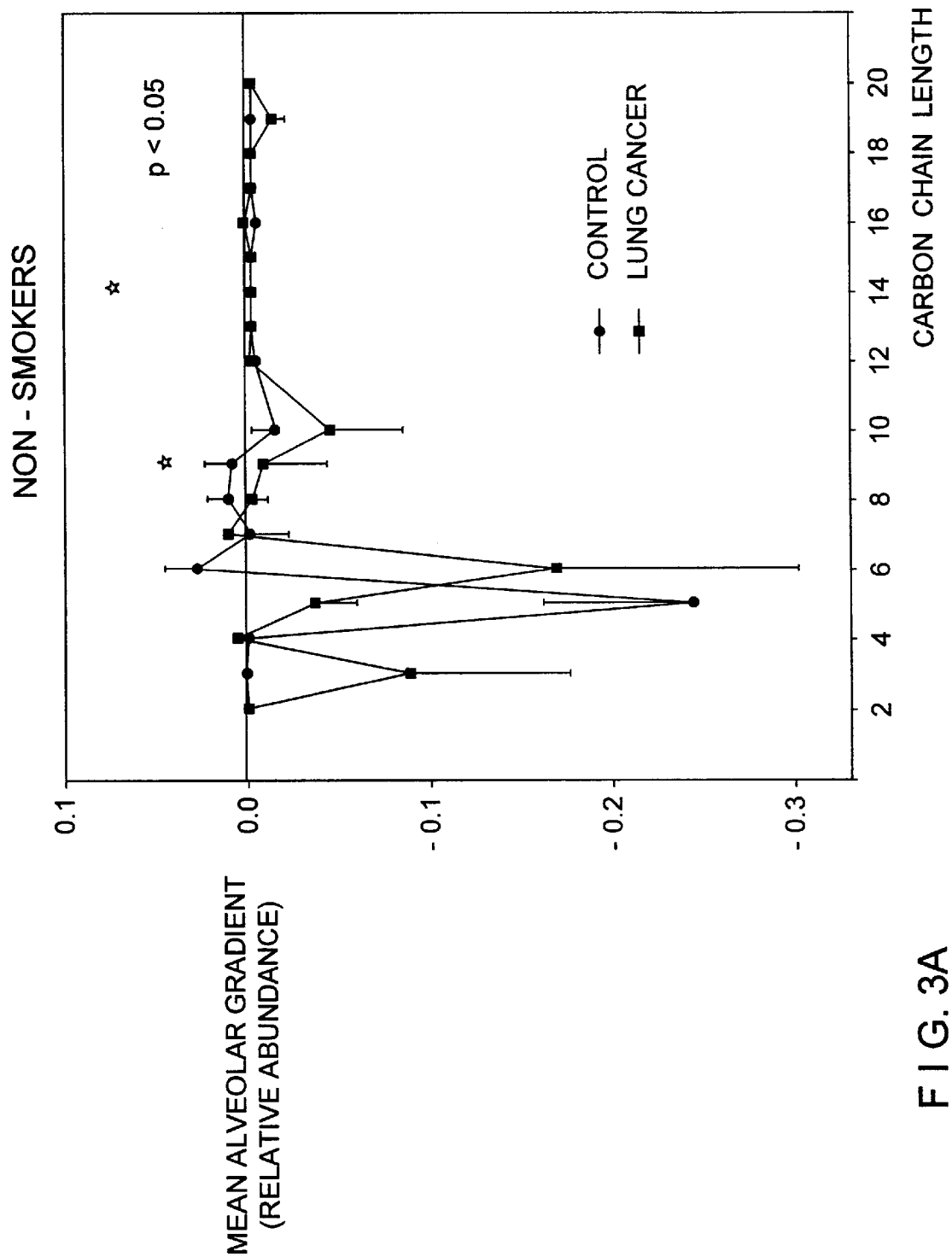
FIG. 3: Effect of smoking status on the breath alkane profile.
Figure 3B:
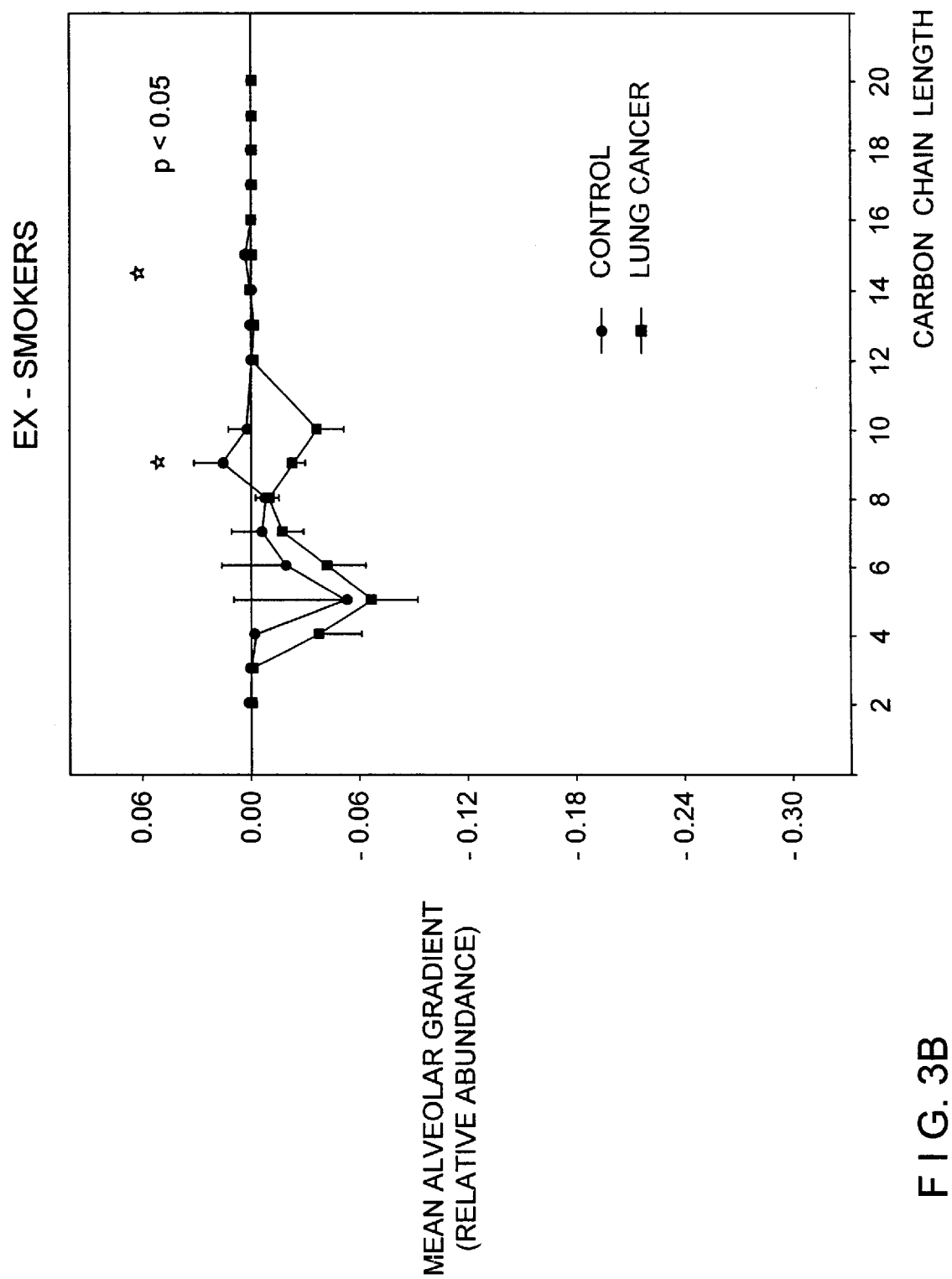
Figure 3C:
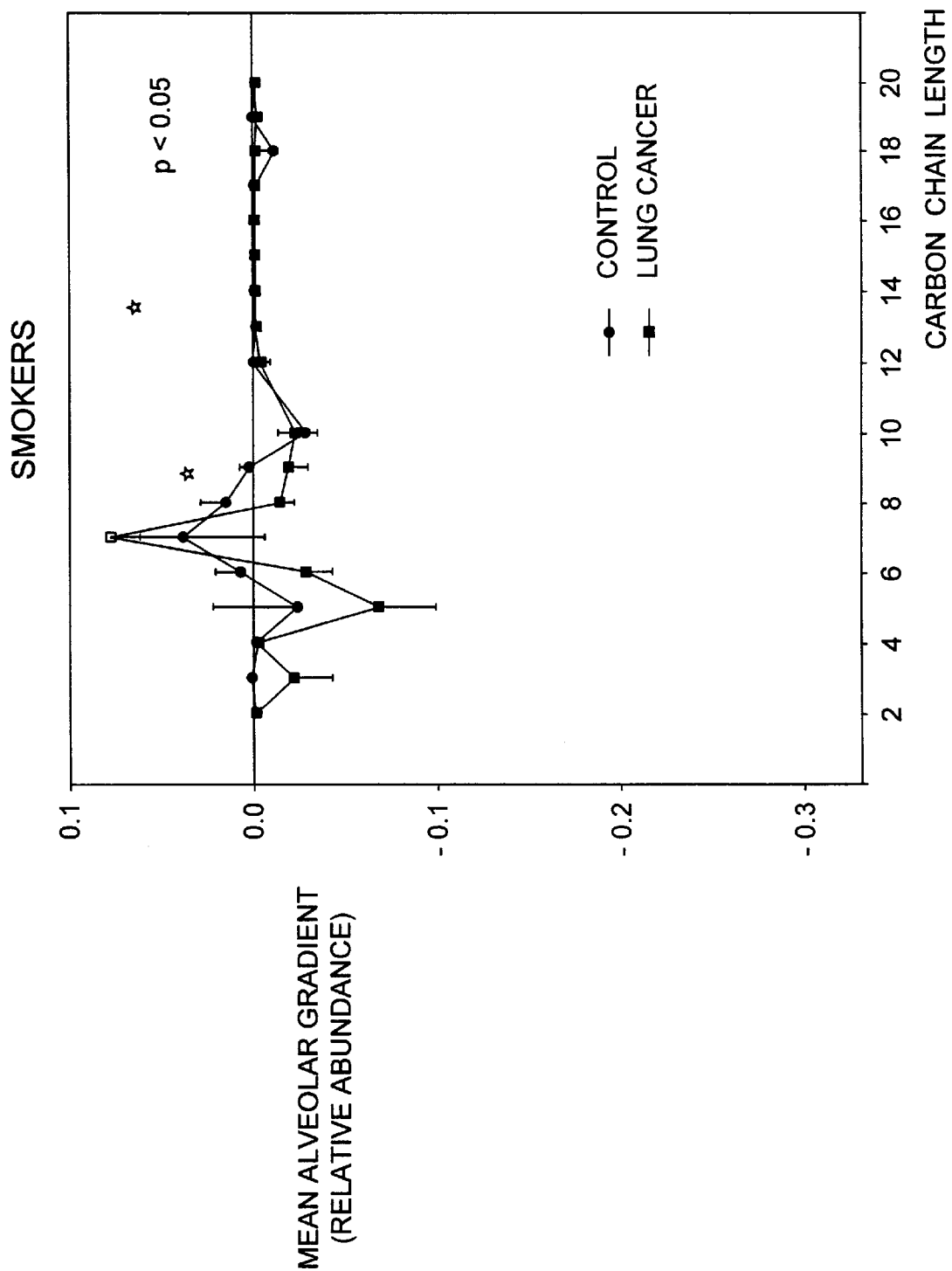

FIG. 3 demonstrates the effect of smoking on the breath alkane profile. The alkane profiles were more elevated in smokers and ex-smokers than in non-smokers. However, the alkane profiles showed differences between lung cancer patients and controls in all three groups, with a statistically significant reduction in nonane in the lung cancer patients. Based on these findings, the breath test was re-evaluated as a test for lung cancer, by analyzing the following variables with logistic regression:

a. Alkane profile plus smoking status b. Alkane profile plus smoking status plus methylalkanes.

The methylalkanes (shown in Table 3) were those identified in the earlier phase of the study as being significantly different in patients with lung cancer.

Figure 4A:
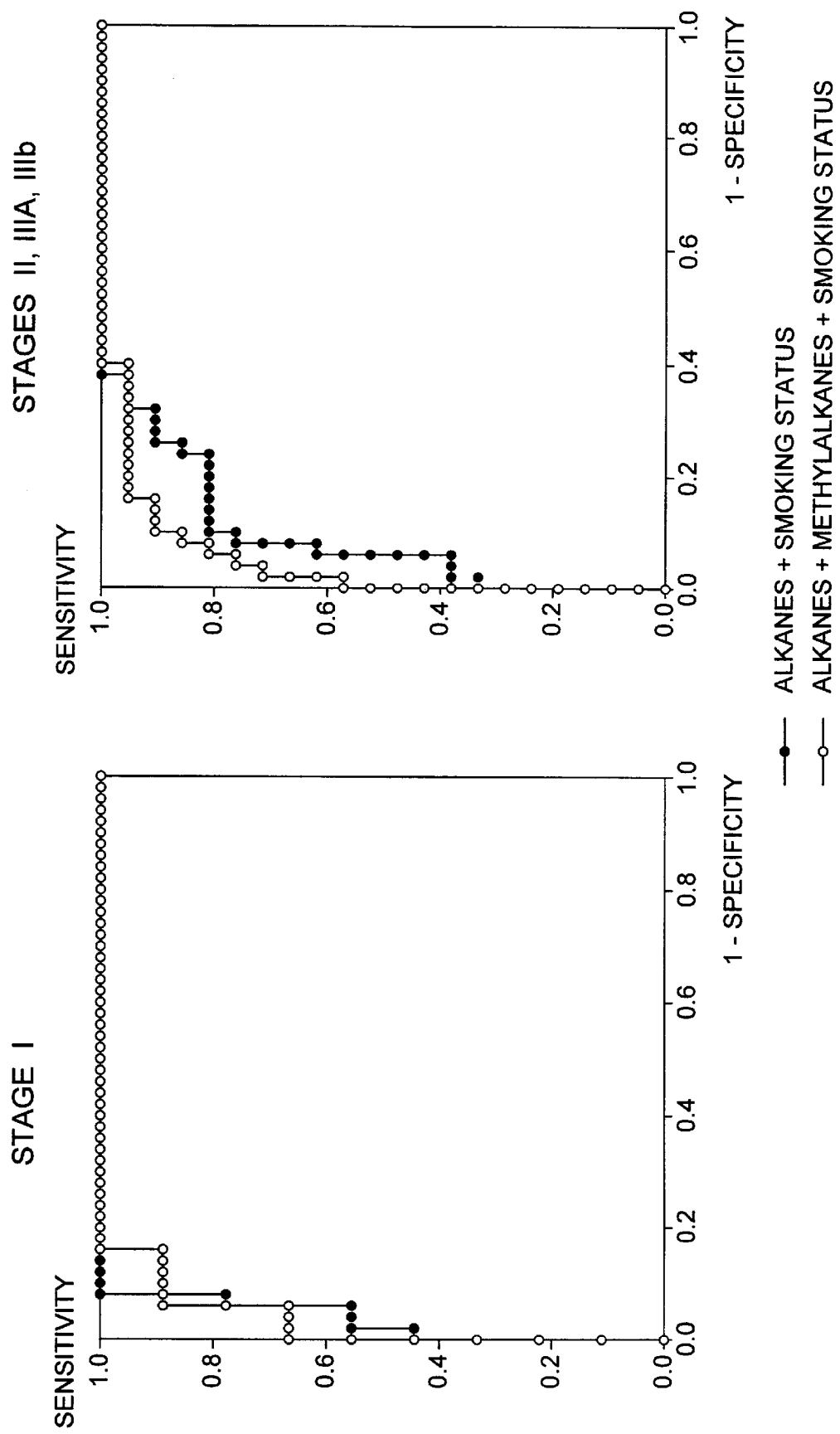
FIG. 4: Results of breath testing in patients with and without lung cancer: These figures demonstrate the sensitivity and specificity of the alkane profile combined with smoking status, and also of the alkane profile combined with smoking status plus the methyl alkanes shown in Table 3.
Figure 4B:
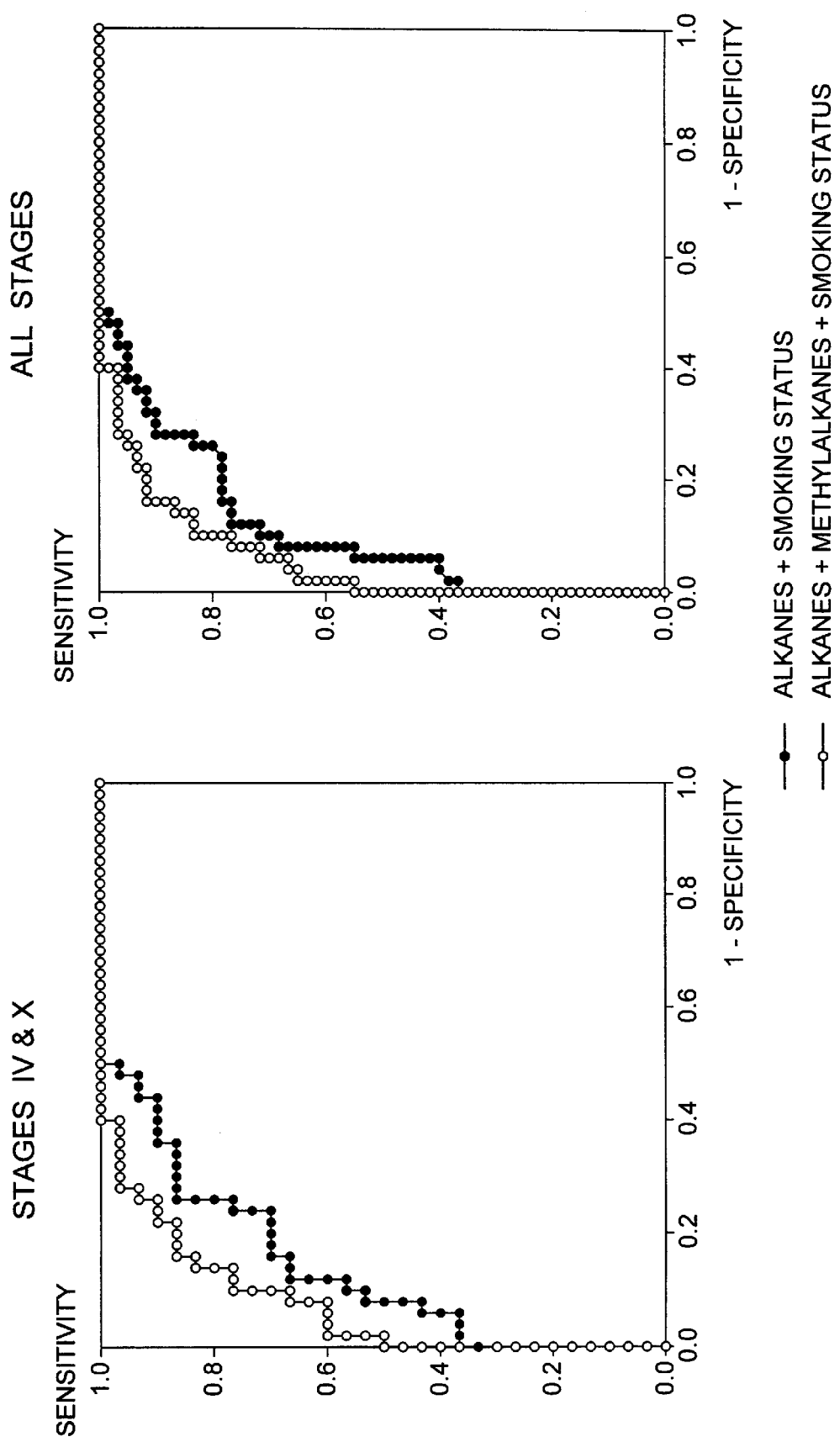

The results of this analysis are shown in FIG. 4 for varius stages of lung cancer. At all stages, the sensitivity and specificity of the test was improved by incorporation of methylalkanes. With the alkane profile alone, sensitivity and specificity were better than 90% in Stages I and II lung cancer.

Figure 5A:
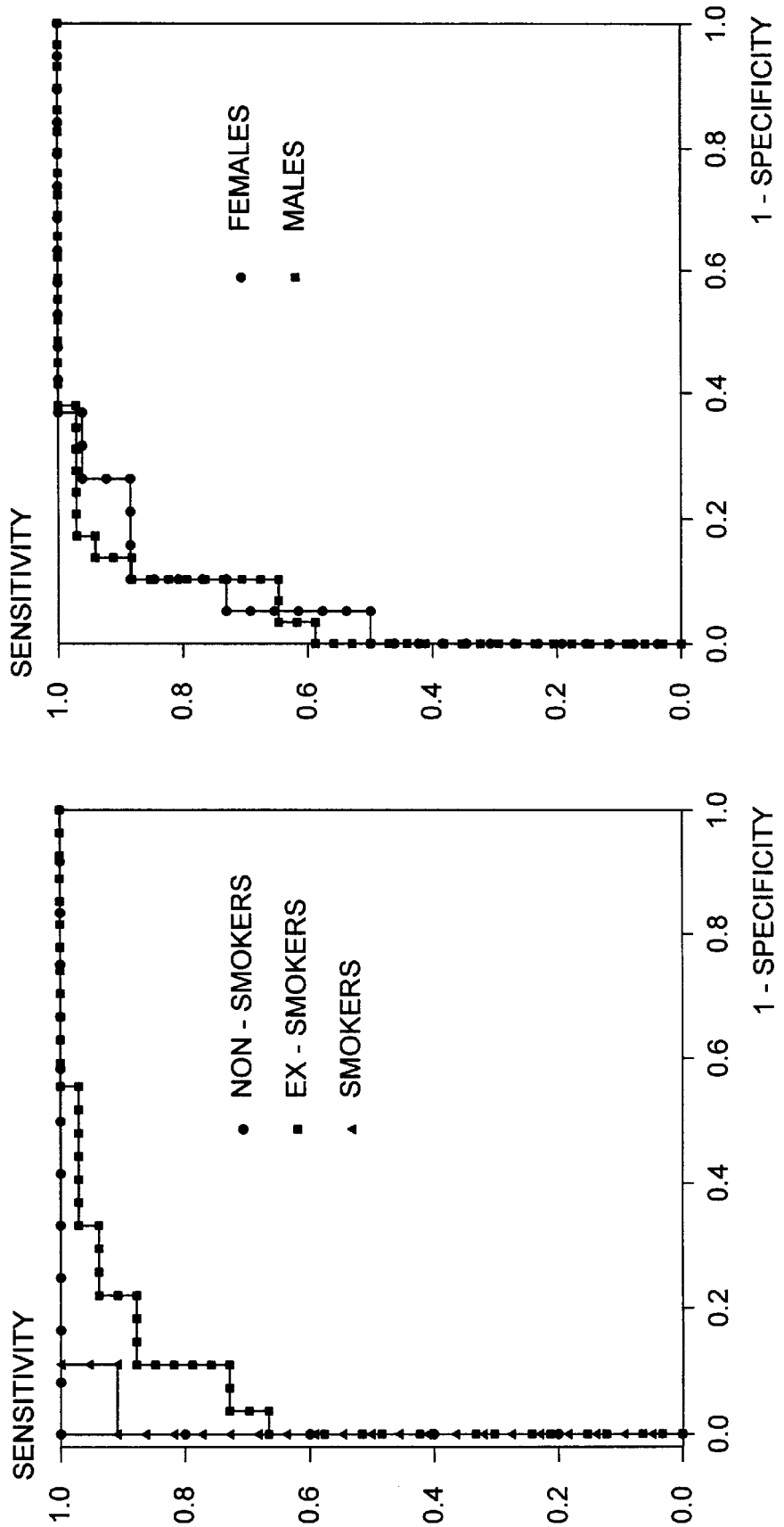
FIG. 5: Performance of the breath test in subgroups: These figures demonstrate the sensitivity and specificity of the alkane profile combined with smoking status plus the methyl alkanes shown in Table 3. The subgroups comprise smoking status, sex, adenocarcinoma and epidermoid carcinoma, and small cell carcinoma and non-small cell carcinoma.
Figure 5B:
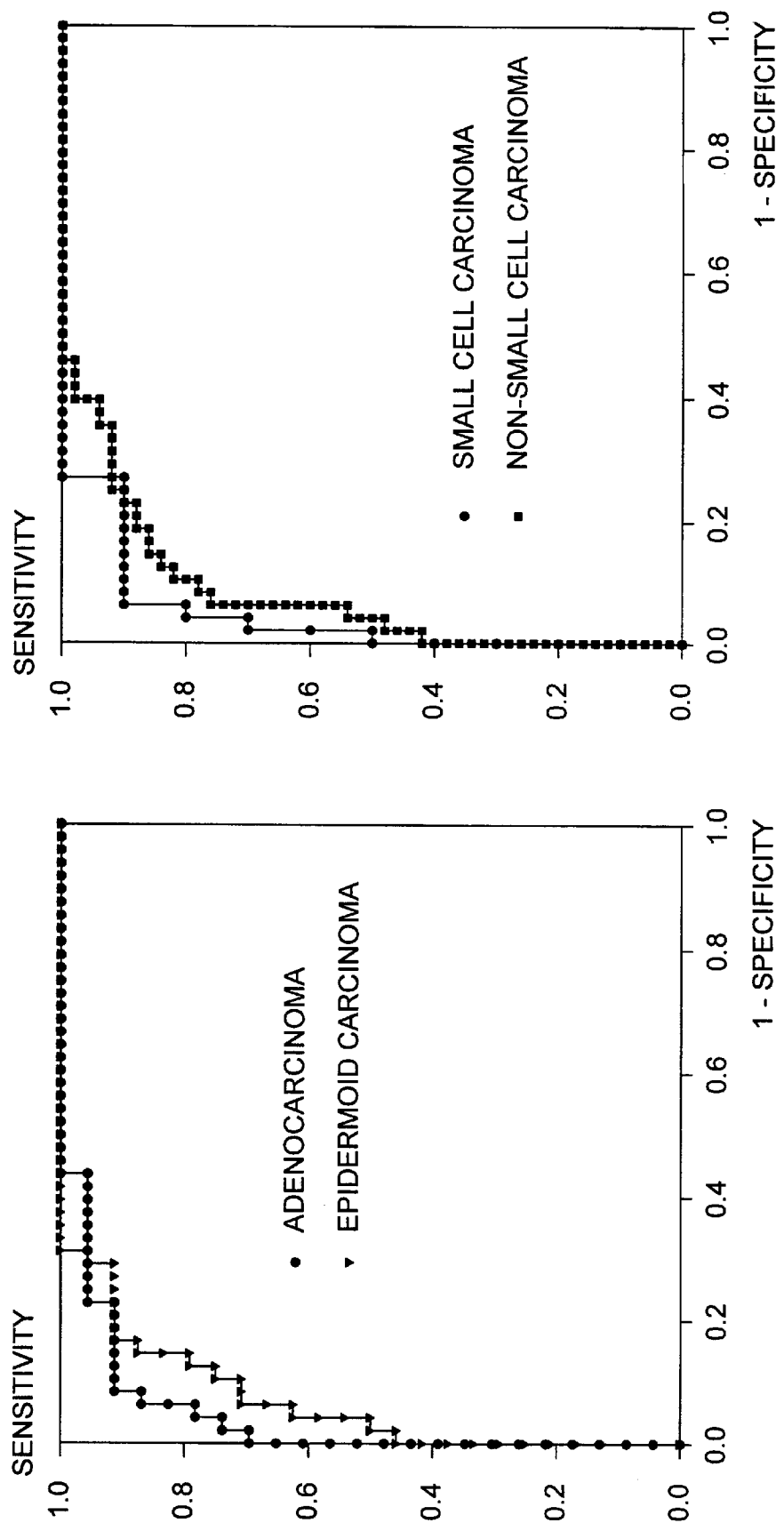

FIG. 5 demonstrates the sensitivity and specificity of the combination of the alkane profile plus smoking status plus methylalkanes in various different groups: patients grouped by smoking status, males versus females, adenocarcinoma and epidermoid carcinoma, and small cell carcinoma and non-small carcinoma. It will be seen that the breath test was highly sensitive and specific for lung cancer in all of these subgroups, and was 100% sensitive and 100% specific in non-smokers.

Figure 6:
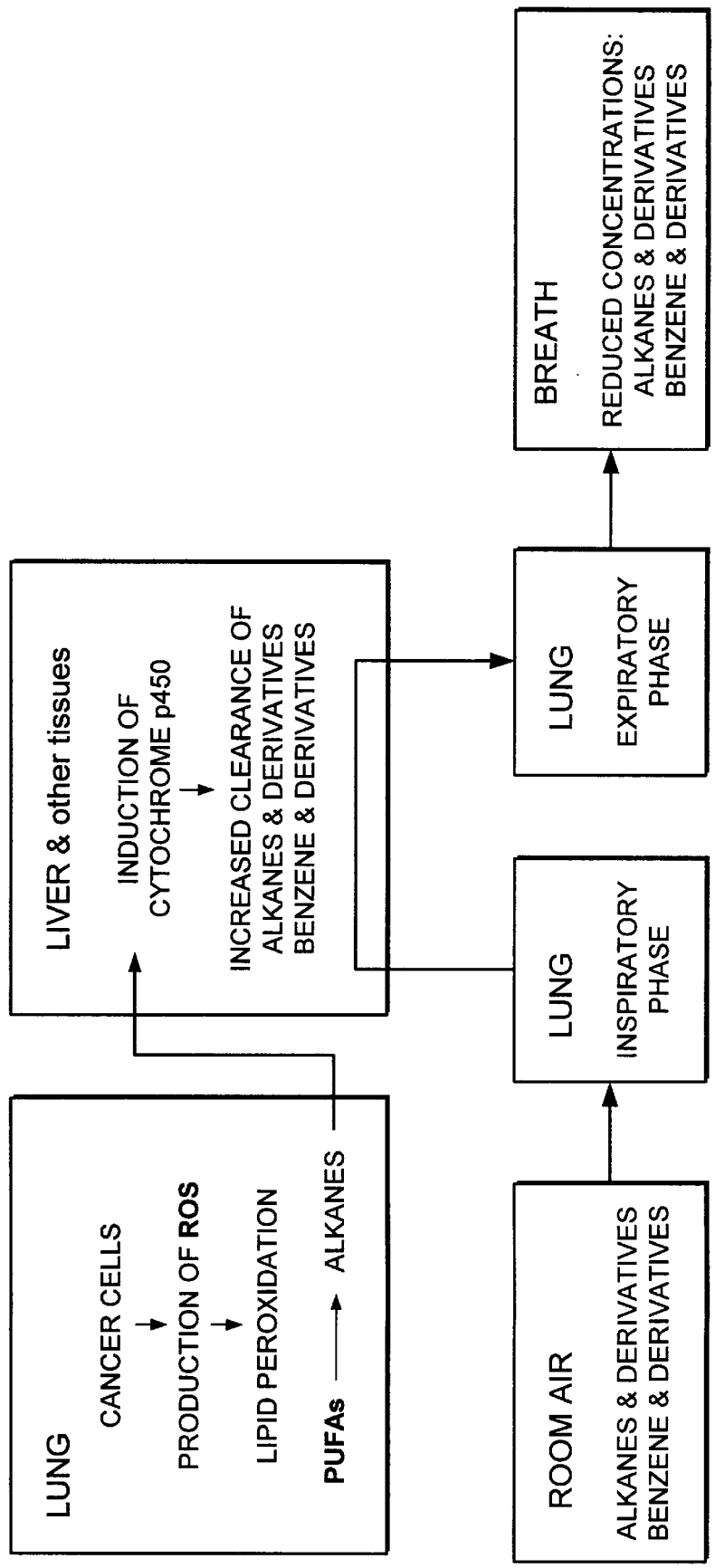
FIG. 6: Proposed mechanism of findings.

The proposed mechanism of these findings is shown in FIG. 6. The possible sequence of events is as follows:

1. Cancer Cells in Lung Produce Reactive Oxygen Species (ROS)

Oxidative stress is the condition caused by increased production of ROS. Clinical studies have demonstrated that oxidative stress is increased in patients with lung cancer, and that it is reduced by surgical removal of the tumor. A similar overproduction of ROS has been observed in lung cancer cells cultured in vitro. In an experimental model of lung cancer, the carcinogen silica was shown to induce increased ROS production in the lung.

2. ROS Cause Peroxidation of PUFAs to Alkanes

ROS are highly reactive, and cause lipid peroxidation of polyunsaturated fatty acids (PUFAs) to alkanes. PUFAs are the main structural components of cell membranes, and this process may result in membrane dysfunction and eventual cell death. The alkanes produced are highly volatile; they enter the circulation and are excreted in the lungs.

3. Circulating Alkanes Induce Cytochrome p450 in Liver and Other Tissues

Animal studies have shown that endogenous and exogenous alkanes are potent inducers of hepatic cytochrome p450 activity. The genes responsible for this response to ambient alkanes have been identified in yeasts.

4. Induced Cytochrome p450 Accelerates Clearance of VOCs in Room Air

Alkanes, methylalkanes, benzene and benzene derivatives are ubiquitous VOCs room air, and are cleared from the body in normal humans. The induced cytochrome p450 enzymes in liver and other tissues accelerate this process, principally by increases in hydroxylation of alkanes, demethylation and transmethylation. Similarly, induced cytochrome p450 enzymes also accelerate the degradation of benzene derivatives. Since clearance is increased, the alveolar gradient of the VOC becomes more negative. Hence, the alkane profile is shifted downwards, and the alveolar gradients of methylalkanes, benzene and methylated benzene derivatives generally become more negative. In a minority of methylated VOCs, the alkane gradient becomes more positive, probably due to increased transmethylation. As a result of these findings, a more preferred group of markers are listed on Table 3.

TABLE 3

Methylalkanes and benzene derivatives employed in combination with alkane profile
Methylalkanes heptane, 2,2,4,6,6-pentamethyl
heptane, 2-methyl
cyclopentane, methyl
octane, 3-methyl
nonane, 3-methyl
heptane, 2,4-dimethyl

What is claimed is:

1. A method of detecting the probable presence of lung cancer in a mammal, including a human, which comprises:

collecting a measured quantity of alveolar breath from the mammal;

analyzing the collected breath for the presence of volatile organic markers for lung cancer;

determining a first mean alveolar gradient for the markers present in the mammal's breath;

comparing the first mean alveolar gradient for the markers present in the mammal's breath to a second mean alveolar gradient for the same markers, found in the breath of a mammal free of lung cancer; and wherein a statistically significant difference in the first mean alveolar gradient from the second mean alveolar gradient indicates the probable presence of lung cancer.

2. A method of detecting the probable presence of lung cancer in a mammal according to claim 1 wherein the volatile organic markers are selected from the group consisting of Styrene (ethenylbenzene); Heptane, 2,2,4,6,6-pentamethyl; Heptane, 2-methyl; Decane; Benzene, propyl-; Undecane; Cyclopentane, methyl-; Cyclopropane, 1-methyl-2-pentyl-; Methane, trichlorofluoro-; Benzene; Benzene, 1,2,4-trimethyl-; 1,3-butadiene, 2-methyl- (isoprene); Octane, 3-methyl-; 1-hexene; Nonane, 3-methyl-; 1-heptene; Benzene, 1,4-dimethyl; Heptane 2,4-dimethyl; Hexanal; Cyclohexane; Benzene, 1-methylethenyl-; and Hepatanal.

3. A method of detecting the probable presence of lung cancer in a mammal according to claim 1 wherein if the mammal is a smoker, then the mammal free of lung cancer is a smoker and if the mammal is not a smoker, then the mammal free of lung cancer is not a smoker and the volatile organic markers are methylalkanes.

4. A method of detecting the probable presence of lung cancer in a mammal according to claim 3 wherein the volatile organic markers are selected from the group consisting of heptane, 2,2,4,6,6-pentamethyl; heptane, 2-methyl; cyclopentane, methyl; octane, 3-methyl; nonane, 3-methyl; and heptane, 2,4-dimethyl.

* * * * *